United States Patent [19]

Rutledge

[11] 4,390,731
[45] Jun. 28, 1983

[54] POLYMERIC PHENOLIC BENZYLIC ETHER COMPOSITIONS

[75] Inventor: Thomas F. Rutledge, Wilmington, Del.

[73] Assignee: ICI Americas Inc., Wilmington, Del.

[21] Appl. No.: 305,147

[22] Filed: Sep. 24, 1981

Related U.S. Application Data

[63] Continuation-in-part of Ser. No. 177,937, Aug. 14, 1980, abandoned.

[51] Int. Cl.³ .................... C07C 43/20; C07C 41/01
[52] U.S. Cl. .................... 568/643; 252/404; 524/339; 528/220; 528/222; 528/98; 528/210
[58] Field of Search .................... 568/643, 730; 260/396 R

[56] References Cited

U.S. PATENT DOCUMENTS 3,210,384 10/1965 Hay .................... 568/643 X

OTHER PUBLICATIONS

Hay, (I) Jour. Org. Chem., vol. 36, No. 1, (1971), 218–219.
Hay, (II) Tetrahedron Letters, No. 47, (1965), 4241–4243.

Primary Examiner—Bernard Helfin

[57] ABSTRACT

Polymeric phenolic benzylic ether compositions are obtained by an intermolecular redox reaction thermolysis of tetraalkyldiphenoquinones at a minimum of about 150° C. The compositions are useful as non-volatile oxidation inhibitors in polymers at high temperatures, as polymerization inhibitors for vinyl monomers, and as crosslinking co-monomers for epoxy and polycarbonate resins.

9 Claims, No Drawings

POLYMERIC PHENOLIC BENZYLIC ETHER COMPOSITIONS

This is a continuation-in-part of application Ser. No. 177,937, filed Aug. 14, 1980 and now abandoned.

FIELD OF THE INVENTION

The present invention relates to polymeric compositions obtained by thermolysis of tetraalkyldiphenoquinones. More particularly, the invention relates to polymeric compositions obtained by reacting at a minimum of about 150° C. a tetraalkyldiphenoquinone of the following formula

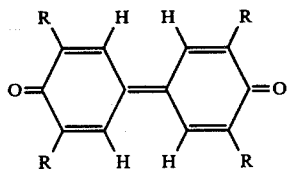

in which R is an alkyl group which contains at least one alpha hydrogen atom. The polymeric compositions comprise units of tetraalkylbiphenol, which are alternately linked through the phenolic oxygen atom, derived from the quinone oxygen atom and the side chain alkyl groups.

DESCRIPTION OF THE PRIOR ART

It is known in the art that diphenoquinones have dehydrogenation activity. It was shown by Tsuruya and Yonezawa in J. Org. Chem. 39, 2438 (1974) that tetramethyldiphenoquinone in benzene irradiated by ultraviolet light yielded small amounts of tetramethylbiphenol and biphenyl, the biphenyl forming from phenyl radicals which are obtained by abstraction of H radicals from the solvent (benzene), the biphenol forming by reduction of the quinone by the H radicals.

When tetraphenyldiphenoquinone is heated at 300° C., an intramolecular redox reaction occurs with H radical abstraction from the phenyl groups to yield, according to Hay, J. Org. Chem. 36, 218 (1971):

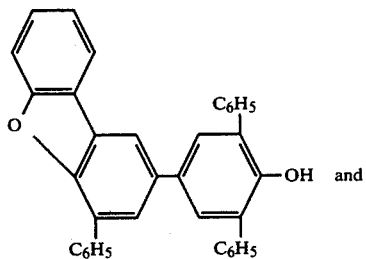

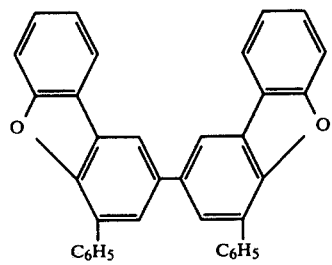

Hay also reported in Tetrahedron Letters 47, 4241 (1965) and in U.S. Pat. No. 3,631,208, that at 100° C. in the presence of an amine catalyst, 1 mole of 3,3',5,5'-tetramethyldiphenoquinone abstracts H radicals from 2 moles of 2,6-xylenol to yield about 2 moles of 3,3',5,5'-tetramethylbiphenol. Also described was the heating of tetra-t-butyl-diphenoquinone with diphenylmethane to yield 1,1,2,2-tetraphenylethane and tetra-t-butyl-biphenol.

It is also known in the art that diphenoquinones can be made to form polymeric condensation products. U.S. Pat. No. 3,959,223 discloses that refluxing 3,3'-di-t-butyldiphenoquinone under nitrogen in chlorobenzene with a copper catalyst yielded:

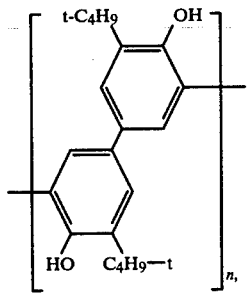

where n=about 15.
Similarly obtained were

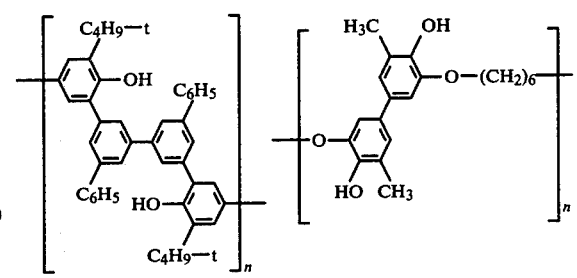

where n=about 40.

A somewhat similar type of polymeric phenolic product is obtained from phenols or novolacs and hydroxymethyl aromatic compounds (aromatic glycols) as described in U.S. Pat. No. 3,384,618 by reactions related to phenol-aldehyde reactions. Bis(hydroxymethyl)benzenes, -naphthalenes, or -anthracenes or polyethers derived from them, such as $HO(CH_2-Ar-CH_2O)_nH$, are heated at 150°–250° C. with a sulfonic acid dehydrating catalyst and a phenol or novolac to yield after a vigorous dehydration reaction, resins embodying alternating units of aromatic glycol and phenol or novolac. The chain formation reaction involves loss of water between the hydroxyl groups of the glycol and the hydrogens on the aromatic nucleus of the phenol.

In summary, the prior art reveals some polymer-forming reactions of phenols and diphenoquinones which proceed via abstraction of hydrogen atoms from hydroxyl groups or from aromatic nuclei or by dehydration reaction between hydroxyl groups and aromatic ring hydrogen atoms.

SUMMARY OF THE INVENTION

In contrast to the prior art, the present invention discloses the discovery that certain tetraalkyldiphenoquinones undergo intermolecular redox reactions when heated at a minimum of 150° C. to form polymeric phenolic benzyl ethers. It is believed that polymer formation proceeds by reaction of the diphenoquinone oxygen atom of one molecule of the tetraalkyldiphenoquinone with a side chain alpha hydrogen on another molecule of tetraalkyldiphenoquinone. The reaction path believed to be followed in the case of tetramethyldiphenoquinone is as exemplified below:

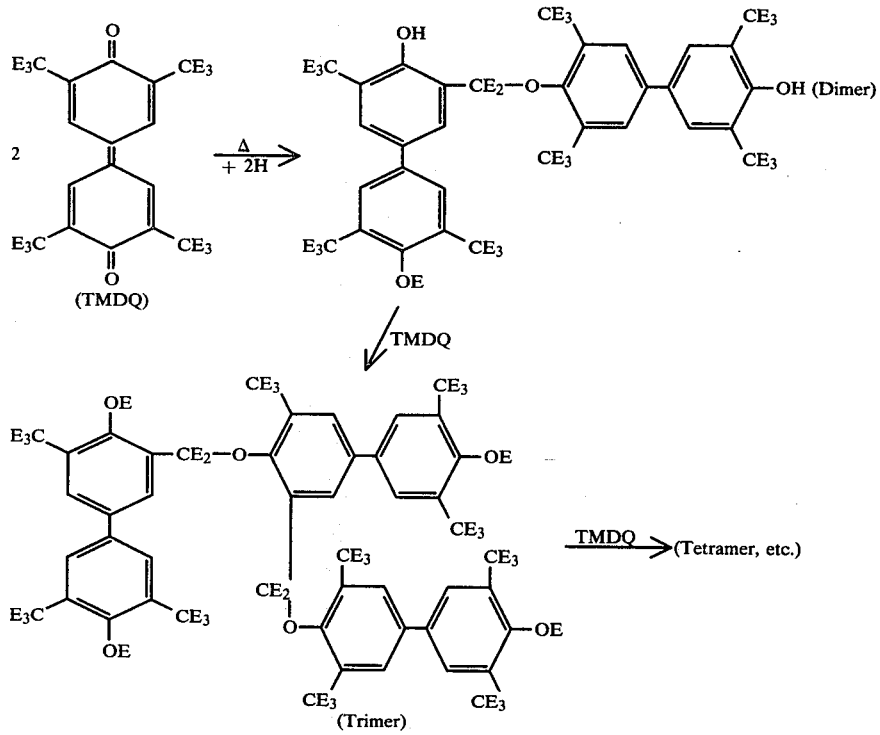

The reaction may occur at any of the other methyl groups instead of those shown above to give a variety of isomeric polymers which are indistinguishable analytically. The presence of benzylic ethers is shown by both infrared and nuclear magnetic resonance spectroscopy. The infrared spectrum differs from that of the starting tetramethyldiphenoquinone in that the methyl group absorption band at 1370 cm.$^{-1}$ is relatively weaker and the methylene band at 1440 cm.$^{-1}$ is stronger than equivalent bands for the diphenoquinone as well as having a diminished and shifted band at 1240, 1350 cm.$^{1}$ which is associated with the phenolic hydroxyl group of the specifically substituted ring of the biphenol. Infrared analysis also indicates that little, if any, carbonyl group is present in the products. Hydroxyl numbers are easily determined and can be used to establish the number of

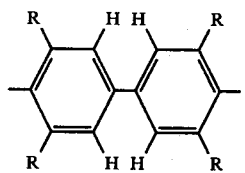

or biphenyl units in a particular polymer.

Instead of methyl groups substituted on the diphenoquinone starting compound as exemplified, there may be present any lower alkyl group so long as there is present at least one side chain alkyl group containing an alpha hydrogen atom, such as ethyl, sec-butyl, isopropyl, etc. Compounds such as dimethyl-di-tert-butyl-diphenoquinone and tetra-sec-butyldiphenoquinone are ths suitable reactants to form the polymers of the invention, while tetra-tert-butyldiphenoquinone is not.

REACTION CONDITIONS

In general, the diphenoquinone may be placed in a reaction vessel and immersed in a fluidized bed heating bath (or other suitable bath) at about 150° to 250° C. for 0.25–2.5 hours. The vessel should then be withdrawn from the bath and cooled to room temperature. The product is a dark red-brown solid. This solid maybe soaked in dilute potassium hydroxide solution, broken up and filtered to give a soluble fraction and an insoluble fraction. The insoluble fraction can be washed with dilute hydrochloric acid, filtered and the solid washed with water, dried and the hydroxyl number determined. The soluble fraction is recovered by acidification to precipitate the polymer. It can then be washed and dried as above. Both product fractions have similar hydroxyl numbers and by infrared spectroscopy both are shown to be benzylic ether polymers.

A preferred reaction which increases the amount of base soluble product comprises the addition of 0.15–2.0 moles of base per mole of diphenoquinone to the vessel. This product, when worked up, has virtually identical infrared and hydroxyl number analysis as the base-insoluble product.

Another preferred reaction procedure includes the presence of a high-boiling point non-reactive organic diluent, such as kerosene, to yield similar products. If a diluent is used, an inert atmosphere such as nitrogen should be used to minimize possible oxidation of the diluent. Diphenyl and diphenyl ether can also be used as diluents when the reaction is run at atmospheric pressure. Other high boiling point non-reactive organic diluents known in the art may also be used.

The benzylic ether polymeric products of the invention are soluble in methanol, acetone, xylene and most of the other common organic solvents.

EXAMPLES

The following examples illustrate the process for preparing the polymers of the invention. In Table I are shown seven examples wherein 4.8 g (20 millimoles) of 3,3′,5,5′-tetramethyl-4,4′-diphenoquinone (TMDQ) is thermolyzed under various indicated conditions. The term units indicates the number of diphenyl nuclei in each polymer.

TABLE I

| Example No. | Base | Mmoles | Atmosphere | T °C. | Hrs | Products Insol. In KOH | | | Sol. in KOH | | |
|---|---|---|---|---|---|---|---|---|---|---|---|
| | | | | | | grams | OH No. | Units | grams | OH No. | Units |
| 1 | None | — | $O_2$ | 200-250 | 1.5 | 2.4 | 342 | 2 | 1.9 | 352 | 2 |
| 2 | KOH | 3 | $O_2$ | 200-245 | 2½ | 0.16 | — | — | 4.2 | 350 | 2 |
| 3 | NaHCO$_3$ | 3 | $O_2$ | 140-250 | 2½ | 0.11 | — | — | 4.9 | 338 | 2 |
| 4 | KOH | 40 | $O_2$ | 205-210 | 2½ | 1.2 | — | — | 3.4 | 273 | 5 |
| 5 | KOH | 40 | $N_2$ | 205-210 | 2½ | 0.4 | — | — | 3.9 | 360 | 2 |
| 6 | KOH | 20(1) | $O_2$ | 210 | 2½ | 0.26 | — | — | 3.96 | 332 | 2 |
| 7 | KOH | 3(2) | $N_2$ | 200-205 | 2½ | 5.11 | 235 | 17 | 5.1 | 353 | 2 |

(1)0.47 mmoles cupric glycinate added
(2)40 mmoles (9.6g) TMDQ, 75 ml Al$_2$O$_3$-treated deobase kerosene as diluent In Table II Examples 8 to 13 include the details of thermolysis of other diphenoquinones under an oxygen atmosphere, 1.5 hours, in the presence of 2.24 g KOH. Units indicates the estimated number of diphenyl nuclei in the polymer derived from the diphenoquinone.

TABLE II

| Example No. | Diphenoquinone | grams | T °C. | Products Soluble In KOH | | | Insoluble In KOH | | |
|---|---|---|---|---|---|---|---|---|---|
| | | | | g | OH No. | Units | g | OH No. | Units |
| 8 | 3,3′-Dimethyl-5,5′ di-t-butyl | 6.48 | 200(1) | 0 | — | — | 6.4(2) | 162 | 12 |
| 9 | 3,3′-Dimethyl-5,5′ di-t-butyl | " | 200 | 0.1 | — | — | 6.31(3) | 220 | 4 |
| 10 | 3,3′-Dimethyl-5,5′ di-t-butyl | " | 240 | 0.21 | — | — | 6.12 | 239 | 3 |
| 11 | 3,3′,5,5′-tetra-sec-butyl | 8.28 | 200 | 2.81(4) | 196 | 2 | 4.82 | 188 | 2 |
| 12 | 3,3′,5,5′-tetra-sec-butyl | " | 240 | 0.7 | — | — | 7.2 | 104 | ~40 |
| 13 | 3,3′,5,5′-tetra-tert-butyl | " | 200 | 0 | — | — | 8.2 | nil | —(5) |

(1)No KOH in charge
(2)m.p. 120-124°
(3)m.p. 135-140°
(4)Sol. MeOH—KOH—H$_2$O
(5)Unreacted tetra-tert-butyldiphenoquinone recovered.

In Table III Examples 14 to 19 samples of about 0.1 grams of TMDQ were placed between two cover glasses and heated for various times to 150° C. or 175° C. After the indicated times the samples were analyzed for TMDQ by visible absorption spectroscopy using a Beckman Model 5240 spectrophotometer with the results shown.

TABLE III

| | | % TMDQ | % Polymeric Composition (by difference) |
|---|---|---|---|
| | | 150° C. | |
| 14 | 0.5 hr | 56.61 | 43.39 |
| 15 | 2 hr | 32.27 | 67.73 |
| 16 | 4 hr | 29.85 | 70.15 |

TABLE III-continued

| | | % TMDQ | % Polymeric Composition (by difference) |
|---|---|---|---|
| | | 175° C. | |
| 17 | 0.5 hr | 18.11 | 81.89 |
| 18 | 2 hr | 1.14 | 98.86 |
| 19 | 4 hr | 0.402 | 99.598 |

Thermolysis products from alkyl-substituted diphenoquinones wherein at least one alpha hydrogen atom is present on the alkyl side chain are effective polymerization inhibitors for vinyl monomers, such as styrene, as shown in Example 15 below.

EXAMPLE 15

Monomer stabilizers are tested by dissolving 0.01% by weight of stabilizer compound in 10 ml volume of the test monomer, such as styrene, in a screw cap test tube, heating the tube to and maintaining it at about 100° C. while nitrogen gas is slowly bubled through the contents of the tube. At the end of each time period about 0.05 g of quinone is added to stop polymerization and the viscosity is measured with a No. 50, No. 100 or No. 200 Ostwald viscometer. The relative viscosity is recorded as the number of seconds to empty a 50 viscometer.

| | RELATIVE VISCOSITY (seconds) | | | |
|---|---|---|---|---|
| Time (min.) | No Stabilizer | Tetramethyl-biphenol | Stabilizer of Example 7 | Stabilizer of Example 9 |
| 0 | 123 | 123 | 123 | 123 |
| 30 | 737.7 | 257.9 | 258 | 318 |
| 60 | 2213 | 1148 | 1138 | 964 |

| RELATIVE VISCOSITY (seconds) | | | | |
|---|---|---|---|---|
| Time (min.) | No Stabilizer | Tetramethyl-biphenol | Stabilizer of Example 7 | Stabilizer of Example 9 |
| 120 | (No. 100)* 9638 (No. 200)* | (No. 100)* 5446 (No. 200)* | 5900 (No. 200)* | (No. 100)* 4440 (No. 200)* |

*Conversion factor to time in seconds between No. 50 and No. 100 viscometer = 3.61, between No. 50 and No. 200 viscometer = 31.05.

Where No. 100 and No. 200 Oswald viscometers are used, the emptying times in seconds are converted by means of predetermined conversion factors to the emptying time for the No. 50 viscometer so as to provide a single basis for comparison of emptying tubes and thus the relative degree of stabilization toward polymerization provided by the various compounds tested.

Since the thermolysis products have a higher molecular weight than the usual commercial products, they are most effective as oxidation inhibitors for polymers at high temperature in that they are not as readily volatilized and lost from the polymers as lower molecular weight oxidation inhibitors are.

The polyfunctionality of the polymers of the invention also makes them useful as crosslinking co-monomers for epoxy resins and polycarbonate polymers.

What is claimed is:

1. The polymeric phenolic benzyl ether composition obtained by heating at a temperature of from about 150° C. to about 250° C. for a period of time of about 0.25 to 2.5 hours an alkyl-substituted diphenoquinone having the formula,

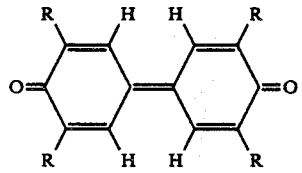

wherein each R is a $C_1$–$C_4$ alkyl group and at least one R group contains an alpha hydrogen atom.

2. A composition of claim 1 wherein each R is methyl.

3. A composition of claim 1 wherein the alkyl-substituted diphenoquinone is heated in the presence of base.

4. A composition of claim 1 wherein the alkyl-substituted diphenoquinone is heated in the presence of an inert high-boiling point diluent under an inert atmosphere.

5. A composition of claim 1 wherein the alkyl-substituted diphenoquinone is heated in the presence of a base, an inert high-boiling point diluent and under an inert atmosphere.

6. A process for obtaining polymeric substituted benzyl ether compositions which comprises heating for a period of time of from about 0.25 to 2.5 hours at a temperature of from about 150° C. to about 250° C. an alkyl-substituted diphenoquinone having the formula,

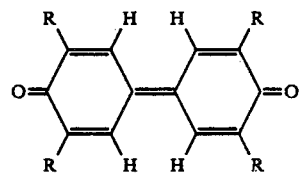

wherein each R is a $C_1$–$C_4$ alkyl group and at least one R group contains an alpha hydrogen atom.

7. A process as claimed in claim 6 wherein the alkyl-substituted diphenoquinone is tetramethyldiphenoquinone.

8. A process as claimed in claim 6 which comprises heating the alkyl-substituted diphenoquinone in the presence of a base selected from the class consisting of potassium hydroxide and sodium bicarbonate.

9. A process as claimed in claim 8 which comprises heating the alkyl-substituted diphenoquinone in the additional presence of an inert high boiling point diluent and under an inert atmosphere.

* * * * *